US012773408B2

(12) United States Patent
Fagrell et al.

(10) Patent No.: US 12,773,408 B2
(45) **Date of Patent: *Oct. 27, 2026**

(54) ANTI-ISCHEMIC COMPOSITIONS

(71) Applicants: Bengt Fagrell, Taby (SE); Jeffrey G. Parker, Wrightwood, CA (US); Nils U. Olsson, San Diego, CA (US)

(72) Inventors: Bengt Fagrell, Taby (SE); Jeffrey G. Parker, Wrightwood, CA (US); Nils U. Olsson, San Diego, CA (US)

(73) Assignees: Bengt Fagrell, Taby (SE); Jeffrey G. Parker, Wrightwood, CA (US); Nils U. Olsson, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/369,023

(22) Filed: Oct. 24, 2025

(65) Prior Publication Data

US 2026/0048057 A1 Feb. 19, 2026

Related U.S. Application Data

(63) Continuation of application No. 17/633,147, filed as application No. PCT/US2020/044905 on Aug. 4, 2020, now Pat. No. 12,472,183.

(60) Provisional application No. 62/882,912, filed on Aug. 5, 2019.

(51) Int. Cl.

| | |
|---|---|
| ***A61K 38/05*** | (2006.01) |
| ***A01N 1/126*** | (2025.01) |
| ***A61K 9/16*** | (2006.01) |
| ***A61K 31/519*** | (2006.01) |
| ***A61K 35/62*** | (2006.01) |
| ***A61K 38/01*** | (2006.01) |
| ***A61K 38/42*** | (2006.01) |
| ***A61P 7/08*** | (2006.01) |
| ***A61P 9/10*** | (2006.01) |

(52) U.S. Cl.

CPC .............. *A61K 31/519* (2013.01); *A61K 9/16* (2013.01); *A61K 38/012* (2013.01)

(58) Field of Classification Search

CPC ...... A61K 38/05; A61K 38/42; A61K 38/012; A61K 9/16; A61K 35/62; A61K 31/519; A61K 2300/00; A61P 7/08; A61P 9/10; A01N 1/126

See application file for complete search history.

(56) References Cited

U.S. PATENT DOCUMENTS

| | | |
|---|---|---|
| 2010/0209902 A1 | 8/2010 | Zal et al. |
| 2014/0113274 A1 | 4/2014 | Dutheil et al. |
| 2015/0190343 A1 | 7/2015 | Hemarina et al. |

FOREIGN PATENT DOCUMENTS

| | | |
|---|---|---|
| WO | 2001056551 A2 | 8/2001 |
| WO | 2021026169 A1 | 2/2021 |

OTHER PUBLICATIONS 5-methyltetrahydrofolate from Medchemexpress.com, pp. 1-3, accessed Feb. 10, 2026 (Year: 2026).*

5-formyltetrahydrofolate from lifeseasons.com, pp. 1-9, accessed Feb. 10, 2026 (Year: 2026).*

5,6,7,8-tetrahydrobiopterin from ThermoFisher.com, pp. 1-4, accessed Feb. 10, 2026 (Year: 2026).*

International Search Report and Written Opinion, mailed Oct. 6, 2020, for International Application Serial No. PCT/US2020/044905 filed Aug. 4, 2020.

Elmer et al., "Oxygen delivery during extreme anemia with ultra-pure earthworm hemoglobin", Life Sciences, vol. 91, No. 2, Oct. 29, 2012, pp. 852-859.

Jani et al., "Polyethylene Glycol Camouflaged Earthworm Hemoglobin", Plos One, vol. 12, Jan. 18, 2017, pp. 1-22.

Maglione et al. "Prevention of lethal murine pancreas ischemia reperfusion injury is specific for tetrahydrobiopterin." Transplant International 25.10 (2012): 1084-1095.

Filpula et al., Releasable PEGylation of proteins with customized linkers, Advanced Drug Delivery Reviews, 2008, 60: 29-49. (2008).

Veronese et al., "PEGylation, successful approach to drug delivery," Drug Discovery Today, Nov. 2005, 10(21): 1451-1458. (2005).

Weber et al., "Nonvertebrate Hemoglobins: FUnctions and Molecular Adaptations," Physiological Reviews, Apr. 2001, 81(2): 569-628. (2001).

* cited by examiner

*Primary Examiner* — Julie Ha

(74) *Attorney, Agent, or Firm* — K&L Gates LLP; Brian J. Novak; David W. Old

(57) ABSTRACT

Described herein are compositions for use in medicine as anti-ischemic organ storage and perfusion solutions.

12 Claims, No Drawings

ANTI-ISCHEMIC COMPOSITIONS

RELATED APPLICATION

This application is a continuation of U.S. patent application Ser. No. 17/633,147, filed Feb. 4, 2022, which is a U.S. national phase of PCT/US2020/044905, filed Aug. 4, 2020, which claims the benefit of U.S. Provisional Ser. No. 62/882,912, filed Aug. 5, 2019, the entire contents of which are incorporated herein by reference.

FIELD

Described herein are compositions for use in medicine as anti-ischemic organ or tissue storage or perfusion solutions.

BACKGROUND

Tissue ischemia is one of the most common causes of morbidity and mortality, and is a major factor in a significant number of donor organs going unused. Current organ storage, preservation and perfusion solutions lack the oxygen carrying capacity of blood. Transplantation surgery involving transportation of the graft tissue or organ currently uses hypothermic preservation techniques (e.g., the tissue or organ is stored in a chest of ice). However, prolonged periods of cold ischemia increase the risk of organ dysfunction and reduce long-term survival. During cold storage of the organ without oxygen perfusion there is a depletion of adenosine triphosphate (ATP) resulting in an intra cellular build-up of toxic substances such as adenosine, inosine and hypoxanthine as well as accumulation of cations and water within the cell causing cellular swelling. One way of alleviating some of these hazards to the organ is to machine perfuse it with a non-oxygen carrying dehydrating solution, such as STEEN Solution™ (Xvivo Perfusion AB Corporation, Sweden), which is an artificial hyper oncotic preparation containing human serum albumin and dextran. Eventually, oxygenated blood flow in the tissue or organ has to be reestablished to prevent cells from dying.

Paradoxically, reperfusion with blood drives pathophysiology and the first minutes of this process are most critical, as the first damaging and irreversible event is a burst of reactive oxygen species (ROS) produced by mitochondria. This ischemia reperfusion injury (IRI) occurs when the blood supply is blocked for a period of time, such as during ex vivo cold storage, shipping from donor to recipient, or machine perfusion with a non-oxygen carrying medium. IRI reduces the bioactivity of 5,6,7,8-tetrahydrobiopterin (BH4). BH4 is a cofactor of endothelial Nitric Oxide Synthase (eNOS) in the production of nitric oxide. With suboptimal levels of BH4, eNOS generates both nitric oxide and superoxide ($O_2^-$), which leads to formation of hydrogen peroxide ($H_2O_2$). Thus, there remains a need for compositions and methods of addressing tissue ischemia in subjects suffering therefrom and in tissue or organs intended for transplantation.

SUMMARY

The compositions described herein can be applied in medicinal applications such as transplantation and surgical interventions that do not include transplantation.

Thus, provided herein are compositions, comprising: a purified erythrocruorin; and 5-methyltetrahydrofolate, 5-formyltetrahydrofolate, 5,6,7,8-tetrahydrobiopterin, or a combination thereof. In some embodiments, poly(ethylene glycol) is covalently attached to the purified erythrocruorin.

Also provided herein are methods of storing a tissue, an organ, an organ cell, or a tissue substitute in need thereof, comprising storing the tissue, organ, organ cell, or tissue substitute, while concurrently contacting the tissue, organ, organ cell, or tissue substitute with a composition provided herein.

Also provided herein are methods of mitigating ischemia in a tissue, an organ, an organ cell, or a tissue substitute in need thereof, comprising contacting the tissue, organ, organ cell, or tissue substitute with a composition provided herein.

Also provided herein are methods of treating ischemia in a subject in need thereof, comprising contacting an ischemic tissue, organ, organ cell, or tissue substitute in the subject with a composition provided herein.

Also provided herein are kits, comprising a composition provided herein.

DETAILED DESCRIPTION

Described herein are compositions for use in medicine as an anti-ischemic organ storage and perfusion solution. The compositions provided herein include: an erythrocruorin (e.g., a purified erythrocruorin); and 5-methyltetrahydrofolate, 5-formyltetrahydrofolate, 5,6,7,8-tetrahydrobiopterin, or a combination thereof. Erythrocruorin is a large acellular Oxygen ($O_2$) Carrying Protein Complex (OCPC) found in organisms such as annelids (e.g., polychaeta, oligochaete (including earthworms, i.e. *Lumbricus terrestris*), or hirudinea) and arthropods (e.g., chilicerata, crustacean, or tracheata). The erythrocruorin of *Lumbricus terrestris*, for example, is an OCPC having a molecular mass over 3.0 million Da (e.g., over 3.5 million Da, e.g., about 3.6 million Da, e.g., about 3.5 million Da). *L. terrestris*'s OCPC (and other erythrocruorins) is not packaged inside a blood cell, like mammalian hemoglobin is. Instead, it floats freely in the liquid that flows through *L. terrestris*'s vascular system.

Thus, provided herein are compositions, comprising: a purified erythrocruorin; and 5-methyltetrahydrofolate, 5-formyltetrahydrofolate, 5,6,7,8-tetrahydrobiopterin, or a combination thereof. In some embodiments, the compositions comprise a purified erythrocruorin, 5-methyltetrahydrofolate, 5-formyltetrahydrofolate, and 5,6,7,8-tetrahydrobiopterin. In some embodiments, the composition is a solid, e.g., a powder. In some embodiments, the composition is a paste. In some embodiments, the composition is a Bingham plastic. In some embodiments, the composition is a freeze-dried powder. In some embodiments, the composition is a liquid. In some embodiments, the composition further comprises a liquid vehicle. In some embodiments, the vehicle is an aqueous vehicle.

In some embodiments, the compositions comprise: a purified erythrocruorin; 5-methyltetrahydrofolate, 5-formyltetrahydrofolate, and 5,6,7,8-tetrahydrobiopterin. In some embodiments, the compositions comprise: a purified erythrocruorin; 5-methyltetrahydrofolate, and 5-formyltetrahydrofolate. In some embodiments, the compositions comprise: a purified erythrocruorin; 5-methyltetrahydrofolate, and 5,6,7,8-tetrahydrobiopterin. In some embodiments, the compositions comprise: a purified erythrocruorin; 5-formyltetrahydrofolate, and 5,6,7,8-tetrahydrobiopterin. In some embodiments, the compositions comprise: a purified erythrocruorin; and 5-methyltetrahydrofolate. In some embodiments, the compositions comprise: a purified erythrocruorin;

and 5-formyltetrahydrofolate. In some embodiments, the compositions comprise: a purified erythrocruorin; and 5,6,7,8-tetrahydrobiopterin.

In some embodiments, the purified erythrocruorin is a purified annelid erythrocruorin (e.g., a polychaeta erythrocruorin, an oligochaete erythrocruorin (including earthworm, i.e. *Lumbricus terrestris*), or a hirudinea erythrocruorin. In some embodiments, the purified erythrocruorin is a purified arthropod erythrocruorin. In some embodiments, the purified erythrocruorin is a purified insect erythrocruorin. In some embodiments, the purified erythrocruorin is a purified *Lumbricus terrestris* erythrocruorin. In some embodiments, the compositions provided herein include a combination of two or more erythrocruorins independently selected from annelid erythrocruorin and arthropod erythrocruorin.

In some embodiments, the composition includes a purified *Lumbricus terrestris* erythrocruorin and 5-methyltetrahydrofolate, 5-formyltetrahydrofolate, 5,6,7,8-tetrahydrobiopterin, or a combination thereof.

In some embodiments, the composition includes a purified *Lumbricus terrestris* erythrocruorin and 5-methyltetrahydrofolate.

In some embodiments, the composition includes a purified *Lumbricus terrestris* erythrocruorin and 5-formyltetrahydrofolate.

In some embodiments, the composition includes a purified *Lumbricus terrestris* erythrocruorin and 5,6,7,8-tetrahydrobiopterin.

In some embodiments, poly(ethylene glycol) is covalently attached to the purified erythrocruorin. In some embodiments, the poly(ethylene glycol) has a molecular weight of about 100 Da to about 60 kDa. In some embodiments, the poly(ethylene glycol) has a molecular weight of about 100 Da to about 200 Da, about 200 Da to about 400 Da, about 400 Da to about 600 Da, about 600 Da to about 800 Da, about 800 Da to about 1 kDa, about 1 kDa to about 2 kDa, about 2 kDa to about 4 kDa, about 4 kDa to about 6 kDa, about 6 kDa to about 8 kDa, about 8 kDa to about 10 kDa, about 10 kDa to about 20 kDa, about 20 kDa to about 30 kDa, about 30 kDa to about 40 kDa, about 40 kDa to about 50 kDa, or about 50 kDa to about 60 kDa. In some embodiments, the poly(ethylene glycol) has a molecular weight of about 100 Da, 200 Da, 400 Da, 600 Da, 800 Da, 1 kDa, 2 kDa, 3 kDa, 4 kDa, 5 kDa, 6 kDa, 7 kDa, 8 kDa, 9 kDa, 10 kDa, 20 kDa, 30 kDa, 40 kDa, 50 kDa, or 60 kDa, or any range there between. In some embodiments, the poly(ethylene glycol) has a molecular weight of about 1 kDa to about 10 kDa, e.g., about 4 kDa to about 6 kDa, e.g., about 5 kDa, In some embodiments, the composition is a pharmaceutical composition. In some embodiments, the pharmaceutical composition includes one or more pharmaceutically acceptable excipients.

Also provided herein are methods of storing tissue, an organ, or an organ cell, comprising storing the tissue, organ or organ cell while concurrently contacting the tissue, organ, or organ cell with a composition provided herein.

Also provided herein are methods of mitigating ischemia in tissue, an organ, or an organ cell in need thereof, comprising contacting the tissue, organ, or organ cell with a composition provided herein.

Also provided herein are methods of preserving tissue, an organ, or an organ cell in need thereof, comprising contacting the tissue, organ, or organ cell with a composition provided herein.

Also provided herein are methods of treating ischemia in a subject in need thereof, comprising contacting ischemic tissue in the subject with a composition provided herein.

In some embodiments of these methods, the subject, tissue, organ, or organ cell is of a mammalian origin. In some embodiments, the subject, tissue, organ, or organ cell is of a human, canine, feline, bovine, ovine, or porcine origin. In some embodiments, the subject, tissue, organ, or organ cell is of a human origin.

In some embodiments, the tissue, organ, organ cell, or tissue substitute is: a lung, liver, or heart tissue; a lung, liver, or heart organ; or a lung, liver, or heart cell. In some embodiments, the tissue, organ, organ cell, or tissue substitute is: a lung, liver, vessel, or heart tissue; a lung, liver, vessel, or heart organ; a lung, liver, vessel, or heart cell; or a lung, liver, vessel, or heart substitute (i.e. a substitute tissue, substitute organ, or substitute cell). In some embodiments, the tissue, organ, organ cell, or tissue substitute is a lung tissue, a lung organ, or a lung cell. In some embodiments, the tissue, organ, organ cell, or tissue substitute is a vessel, a vessel cell, or a vessel substitute. In some embodiments, the tissue substitute is a lung, liver, vessel, or heart tissue substitute. In some embodiments, the organ is a lung, liver, vessel, or heart.

In some embodiments, the tissue, organ, organ cell, or tissue substitute is a tissue. In some embodiments, the tissue, organ, organ cell, or tissue substitute is an organ. In some embodiments, the tissue, organ, organ cell, or tissue substitute is an organ cell. In some embodiments, the tissue, organ, organ cell, or tissue substitute is a tissue substitute.

In some embodiments, the tissue substitute is a biomaterial or composite scaffolded for, e.g., lung or cardiac tissue engineering, perfusable patches (grafts), or hearts (including other organs (e.g., lung) or grafts), made with or without 3-D printing or nano technology.

In some embodiments, the methods described herein are performed at about 0-39° C. In some embodiments, these methods are performed at about 10-39° C. In some embodiments, these methods are performed at about 5-15° C. In some embodiments, these methods are performed at about 10-25° C. In some embodiments, these methods are performed at about 15-25° C. In some embodiments, these methods are performed at about 15-37° C. In some embodiments, these methods are performed at about 25-39° C. In some embodiments, these methods are performed at about 25-37° C. In some embodiments, these methods are performed at about 35-39° C. In some embodiments, these methods are performed at about 37-39° C. In some embodiments, these methods are performed at about 0° C. In some embodiments, these methods are performed at about 5° C. In some embodiments, these methods are performed at about 37° C. In some embodiments, these methods are performed at about 10° C. In some embodiments, these methods are performed at about 15° C. In some embodiments, these methods are performed at about 20° C. In some embodiments, these methods are performed at about 25° C. In some embodiments, these methods are performed at about 30° C. In some embodiments, these methods are performed at about 35° C. In some embodiments, these methods are performed at about 36° C. In some embodiments, these methods are performed at about 37° C. In some embodiments, these methods are performed at about 38° C. In some embodiments, these methods are performed at about 39° C.

In some embodiments, the compositions provided herein can remain in an oxygenated state by circulating the composition through an oxygenator pump mechanism connected to an extracorporeal tissue, organ, organ cell, or tissue substitute. The tissue, organ, organ cell, or tissue substitute can thereby also remain in an oxygenated state when in contact with such circulating composition. In some embodiments, the compositions can be used alone or in combination with standard perfusion solutions, colloids, crystalloids, plasma expanders, e.g., albumin, volume expanders, e.g., Voluven, and isotonic large-volume fluid replacement solutions, e.g., Ringer's Lactate or Ringer's Acetate solutions.

Also provided herein are kits, comprising a composition provided herein.

EXAMPLES

The following examples illustrate the compositions and uses described herein.

Example 1: Preparation of Erythrocruorin Compositions

The Oxygen Carrying Protein Complex (OCPC) is isolated from terrestrial earthworms (nightcrawlers, a.k.a. *Lumbricus terrestris*) and purified by tangential-flow filtration following the procedure described by J. P. Elmer in Life Sciences, 2012, 91, 852-9. Approximately 10 g of OCPC is isolated per 1,000 worms. The isolated OCPC is stored as a liquid solution, or lyophilized to a powder that can be reconstituted as a liquid.

Example 2: Preparation of Erythrocruorin Compositions Including Micronutrients The isolated OCPC of Example 1 is combined with micronutrient(s). Thus, the isolated OCPC is combined with 0.001 to 500 μmol/L 5-methyltetrahydrofolate and 0.001 to 500 μmol/L 5,6,7,8-tetrahydrobiopterin. The resulting mixture is stored as a liquid, reduced to a paste, or lyophilized to a powder that can be reconstituted as a liquid.

Example 3: Preparation of Erythrocruorin Compositions Including Micronutrients The isolated OCPC of Example 1 is combined with micronutrient(s). Thus, the isolated OCPC is combined with 0.001 to 500 μmol/L 5-formyltetrahydrofolate and 0.001 to 500 μmol/L 5,6,7,8-tetrahydrobiopterin. The resulting mixture is stored as a liquid, reduced to a paste, or lyophilized to a powder that can be reconstituted as a liquid.

Example 4: Preservation of Organ or Tissue

An organ (e.g., a lung, liver or heart) is contacted with the liquid composition of Example 2, 3, or 6 at body temperature. The organ's metabolic activities are preserved while in contact with the liquid composition.

Example 5: Preservation of Organ or Tissue

An organ (e.g., a lung, liver or heart) is contacted with the liquid composition of Example 3 at body temperature. The organ's metabolic activities are preserved while in contact with the liquid composition.

Example 6: Preparation of Erythrocruorin Compositions Including Micronutrients The isolated OCPC of Example 1 is combined with micronutrient(s). Thus, the isolated OCPC is combined with 0.001 to 500 μmol/L 5-methyltetrahydrofolate, 0.001 to 500 μmol/L 5-formyltetrahydrofolate, and 0.001 to 500 μmol/L 5,6,7,8-tetrahydrobiopterin. The resulting mixture is stored as a liquid, reduced to a paste, or lyophilized to a powder that can be reconstituted as a liquid.

Although preferred embodiments have been described in this specification and the accompanying drawings, it will be appreciated that a number of variations and modifications may suggest themselves to those skilled in the pertinent arts. Thus, the scope of the present disclosure is not limited to the specific embodiments and examples described herein, but should be deemed to encompass alternative embodiments and equivalents.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the compositions and methods described herein (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the present disclosure and does not pose a limitation on the scope of the disclosure otherwise claimed. No language in the specification should be construed as indicating any non-claimed element essential to the use of the compositions and methods provided herein.

Groupings of alternative elements or embodiments of the compositions and methods disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of these compositions and methods are described herein, including the best mode known to the inventors for carrying out the present disclosure. Of course, variations on these described embodiments will become apparent to those of ordinary skill in the art upon reading the foregoing description. The inventor(s) expect(s) skilled artisans to employ such variations as appropriate, and the inventor(s) intend(s) for the compositions and methods described herein to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the compositions and methods disclosed herein are illustrative of the principles of the present disclosure. Other modifications that may be employed are within the scope of the present disclosure. Thus, by way of example, but not of limitation, alternative configurations of the present disclosure may be utilized in accordance with the teachings herein. Accordingly, the present disclosure is not limited to that precisely as shown and described.

What is claimed is:

1. A method of preparing a composition, wherein the method comprises:

mixing, in an aqueous liquid vehicle, (a) a purified erythrocruorin with (b) a solution comprising 5-methyltetrahydrofolate, 5-formyltetrahydrofolate, or a combination thereof, and optionally (c) a solution comprising 5,6,7,8-tetrahydrobiopterin, to form an aqueous liquid solution comprising the composition.

2. The method of claim 1, wherein the method further comprises lyophilizing the aqueous liquid solution to a powder.

3. The method of claim 1, wherein the method comprises:

mixing the purified erythrocruorin with 5-methyltetrahydrofolate and 5,6,7,8-tetrahydrobiopterin at concentrations of 0.001 to 500 μmol/L of the aqueous liquid solution.

4. The method of claim 3, wherein the method further comprises lyophilizing the aqueous liquid solution to a powder.

5. The method of claim 1, wherein the method comprises:

mixing the purified erythrocruorin with 5-formyltetrahydrofolate and 5,6,7,8-tetrahydrobiopterin tetrahydrobiopterin at concentrations of 0.001 to 500 μmol/L of the aqueous liquid solution.

6. The method of claim 5, wherein the method further comprises lyophilizing the aqueous liquid solution to a powder.

7. The method of claim 1, wherein the method comprises:

mixing the purified erythrocruorin with 5-methyltetrahydrofolate, 5-formyltetrahydrofolate and 5,6,7,8-tetrahydrobiopterin at concentrations of 0.001 to 500 μmol/L of the aqueous liquid solution.

8. The method of claim 7, wherein the method further comprises lyophilizing the aqueous liquid solution to a powder.

9. The method of claim 1, wherein the purified erythrocruorin is a purified annelid erythrocruorin.

10. The method of claim 1, wherein the purified erythrocruorin is a purified arthropod erythrocruorin.

11. The method of claim 1, wherein the purified erythrocruorin is a purified insect erythrocruorin.

12. The method of claim 1, wherein the purified erythrocruorin is a purified *Lumbricus terrestris* erythrocruorin.

* * * * *